United States Patent [19]

Kelman

[11] Patent Number: 5,606,798
[45] Date of Patent: Mar. 4, 1997

[54] HAIR CUTTING APPARATUS

[76] Inventor: Elliot Kelman, 44 Western Avenue, London, England, NW11 9PR

[21] Appl. No.: 946,380

[22] PCT Filed: Mar. 10, 1992

[86] PCT No.: PCT/GB92/00426

§ 371 Date: Jan. 8, 1993

§ 102(e) Date: Jan. 8, 1993

[87] PCT Pub. No.: WO92/16338

PCT Pub. Date: Oct. 1, 1992

[30] Foreign Application Priority Data

Mar. 12, 1991 [IL] Israel .......................................... 97531

[51] Int. Cl.⁶ ..................................................... B26B 19/44
[52] U.S. Cl. ............................. 30/41.5; 30/41.6; 219/223
[58] Field of Search .................................... 30/41.5, 41.6; 219/121.61, 121.67, 121.72, 121.74, 223; 132/200

[56] References Cited

U.S. PATENT DOCUMENTS

| | | |
|---|---|---|
| 1,378,137 | 5/1921 | Ross . |
| 1,720,715 | 7/1929 | Welden . |
| 3,093,724 | 6/1963 | Johnson ........................... 219/29 |
| 3,197,612 | 5/1963 | Reich ............................... 219/223 |
| 3,659,613 | 5/1972 | Bredemeier ..................... 128/395 |
| 3,693,623 | 9/1972 | Harte et al. ................... 128/303.1 |
| 4,051,760 | 10/1977 | Glennan . |
| 4,089,110 | 5/1978 | Rasco ............................... 30/41.6 |
| 4,388,924 | 6/1983 | Weissman ..................... 128/303.1 |
| 4,578,558 | 3/1986 | Clegg . |
| 4,819,669 | 4/1989 | Politzer .......................... 219/223 |
| 5,037,183 | 8/1991 | Gagosz et al. ................ 219/121.72 |
| 5,038,015 | 8/1991 | Einav et al. .................. 219/121.67 |
| 5,043,553 | 8/1991 | Corfe et al. .................. 219/121.67 |
| 5,065,515 | 11/1991 | Iderosa ............................ 132/200 |
| 5,079,402 | 1/1992 | Arai .............................. 219/121.74 |
| 5,093,549 | 3/1992 | Iwai et al. ..................... 219/121.74 |

FOREIGN PATENT DOCUMENTS

| | | |
|---|---|---|
| 2123287 | 2/1984 | United Kingdom . |
| 9106406 | 5/1991 | WIPO . |

Primary Examiner—Richard K. Seidel
Attorney, Agent, or Firm—Ladas & Parry

[57] ABSTRACT

Hair cutting apparatus including a housing and laser apparatus disposed in the housing and arranged to provide a beam of light impinging on hair to be cut, the beam of light being operative to cut the hair.

1 Claim, 5 Drawing Sheets

HAIR CUTTING APPARATUS

The present invention relates to hair cutting apparatus generally.

BACKGROUND OF THE INVENTION

There exists a great variety of hair cutting apparatus. These include single or multiple blade razors which are pulled across the surface of the skin and devices having an electrically powered vibratory element which drives opposing blades in a scissors type action.

U.S. Pat. No. 3,934,115 describes a method and apparatus for electric single cutting in which heated and opposed edges of two thin strips of metal form a slot, at which hair extending therethrough is singed to effect severance of the hair.

SUMMARY OF THE INVENTION

The present invention seeks to provide improved hair cutting apparatus.

There is thus provided in accordance with a preferred embodiment of the present invention hair cutting apparatus including a housing and laser apparatus disposed in the housing and arranged to provide a beam of light impinging on hair to be cut, the beam of light being operative to cut the hair.

In accordance with a preferred embodiment of the present invention, the laser apparatus is operative to provide a beam of light at a wavelength which is strongly absorbed by hair to be cut but not strongly absorbed by adjacent tissue.

In accordance with a preferred embodiment of the present invention, the wavelength of the beam is such that it is generally not absorbed by human skin.

A preferred wavelength range for operation of the shaving operation is 0.8 micron.

In accordance with a preferred embodiment of the invention the operational wavelength of the laser apparatus is selected to be such that only hairs of a certain color, such as white or gray hairs, are cut and the remainder of the hairs are not cut. A wavelength of 0.8 micron is suitable for this purpose. Such apparatus may be particularly useful for removing unwanted white or gray hairs automatically.

In accordance with a preferred embodiment of the present invention, the laser apparatus also comprises optical transfer means for directing the beam to the hair. The optical transfer means may include refraction and reflection means having optical power.

Additionally in accordance with a preferred embodiment of the invention, hair collection apparatus may also be provided in the housing for collecting loose hairs that have been cut by the laser beam. The hair collection apparatus may comprise a vacuum device or alternatively or additionally, electrostatic hair collection apparatus.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1A:
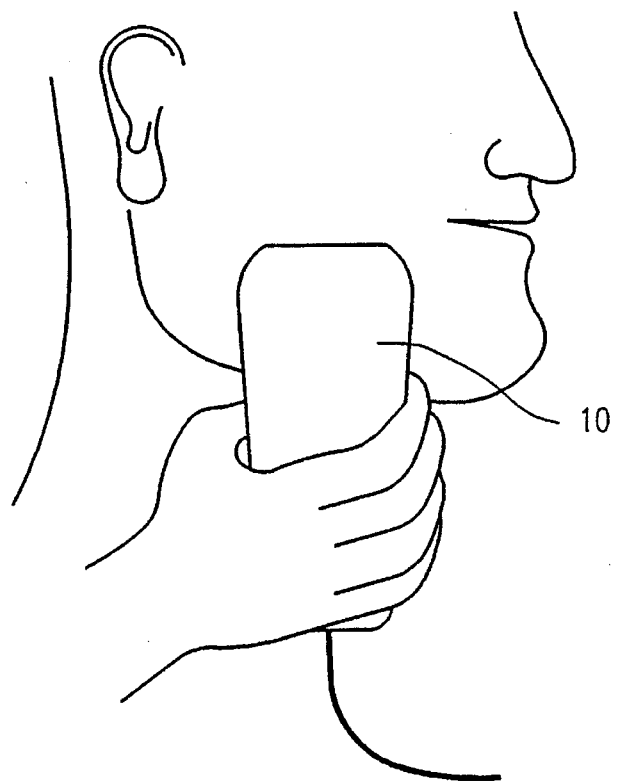
FIG. 1A is a pictorial illustration of the use of a shaver constructed and operative in accordance with a preferred embodiment of the present invention.
Figure 1B:
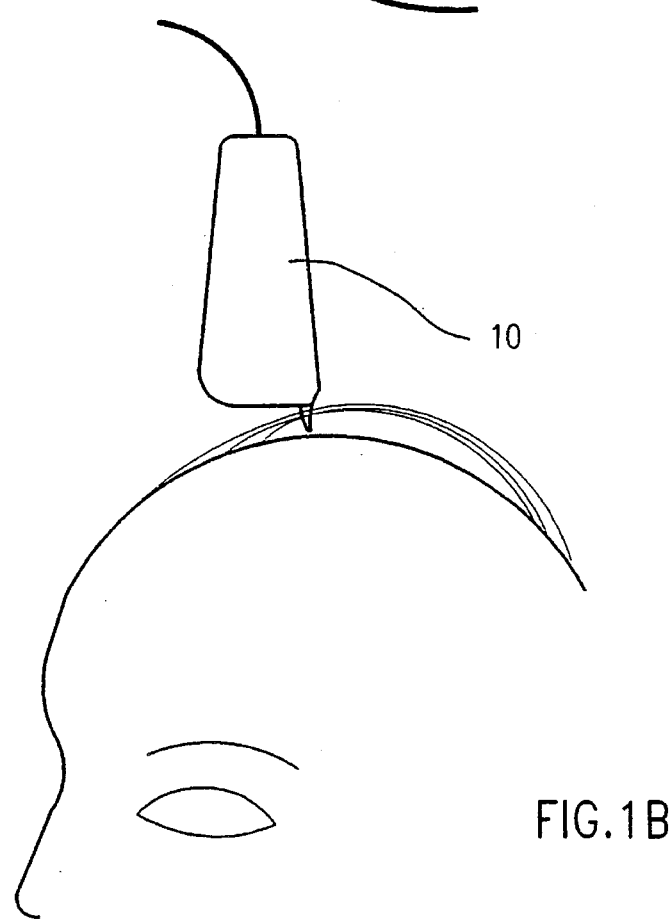
FIG. 1B is a pictorial illustration of the use of a laser hair cutter constructed and operative in accordance with a preferred embodiment of the present invention.
Figure 2A:
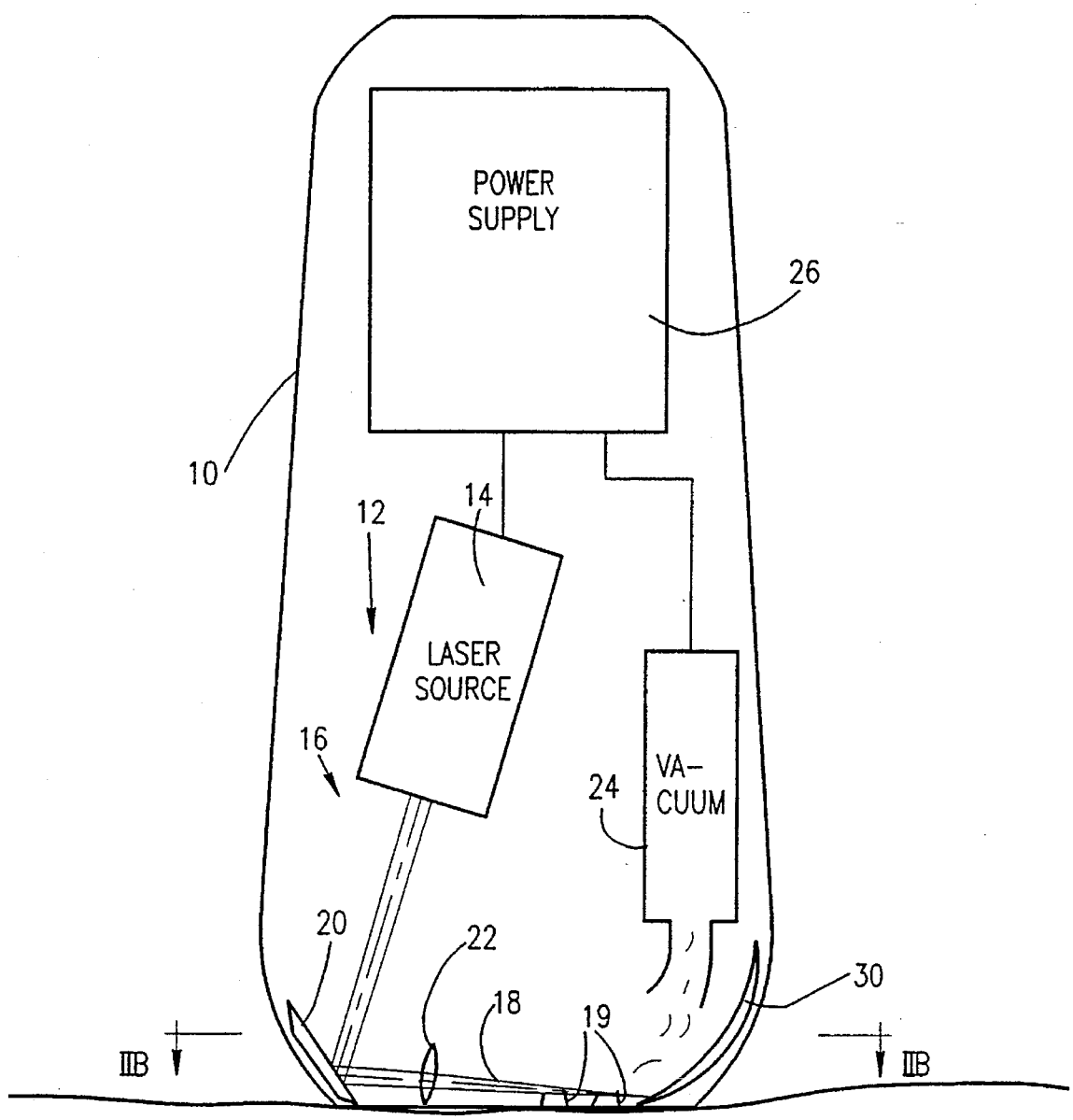
FIG. 2A is a simplified sectional illustration of a laser shaver constructed and operative in accordance with a preferred embodiment of the present invention.
Figure 2B:
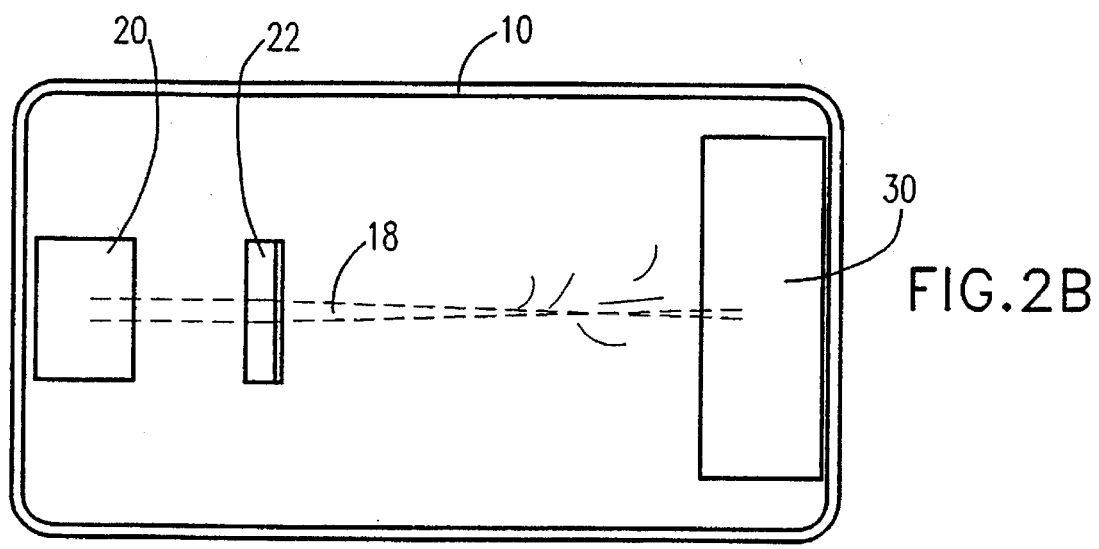
FIG. 2B is a simplified sectional illustration taken along the lines 2B—2B of FIG. 2A.

Reference is now made to FIGS. 1A, 2A and 2B which illustrate a laser shaver constructed and operative in accordance with a preferred embodiment of the present invention. The laser shaver preferably comprises a housing 10, typically formed of plastic or of any other suitable material. Disposed within housing 10 is a laser apparatus 12, preferably comprising a laser source 14 and laser beam transfer optics 16, which direct a laser beam 18, produced by the laser source 14 to hairs 19 to be cut.

In accordance with a preferred embodiment of the present invention, the laser source 14 comprises a semiconductor laser such as a Gallium Arsenide laser, preferably operative to provide an output laser beam at a wavelength which is strongly absorbed by hair, such as facial hair but which is not strongly absorbed by surrounding tissue, such as skin. A preferred wavelength is 0.8 microns, although it is assumed that other wavelengths may also be suitable.

It is a particular feature of the present invention that suitable selection of the operative wavelength of the laser source 14 enables hair to be vaporized and carbonized at the location of impingement of the laser beam 18 thereon, thus separating that portion of the hair still attached to the hair follicle from that extending outward from the impingement location, thereby producing a hair cutting effect.

It is also a particular feature of the present invention that by suitable selection of the operative wavelength of the laser source only hair of a selectable color or range of colors may be cut, while hairs of other colors are left intact. In such a way white or gray hairs may be automatically removed by a simple combing action.

The laser beam transfer optics 16 preferably comprise reflective optics, such as a mirror 20 and refractive optics such as a lens 22. Any other suitable arrangement of laser beam transfer optics 16, including any suitable optical element or elements may alternatively be employed.

In accordance with one preferred embodiment of the present invention, there is also provided a laser beam absorber 30 for absorbing the laser beam and thus preventing spurious impingements thereof.

Figure 3A:
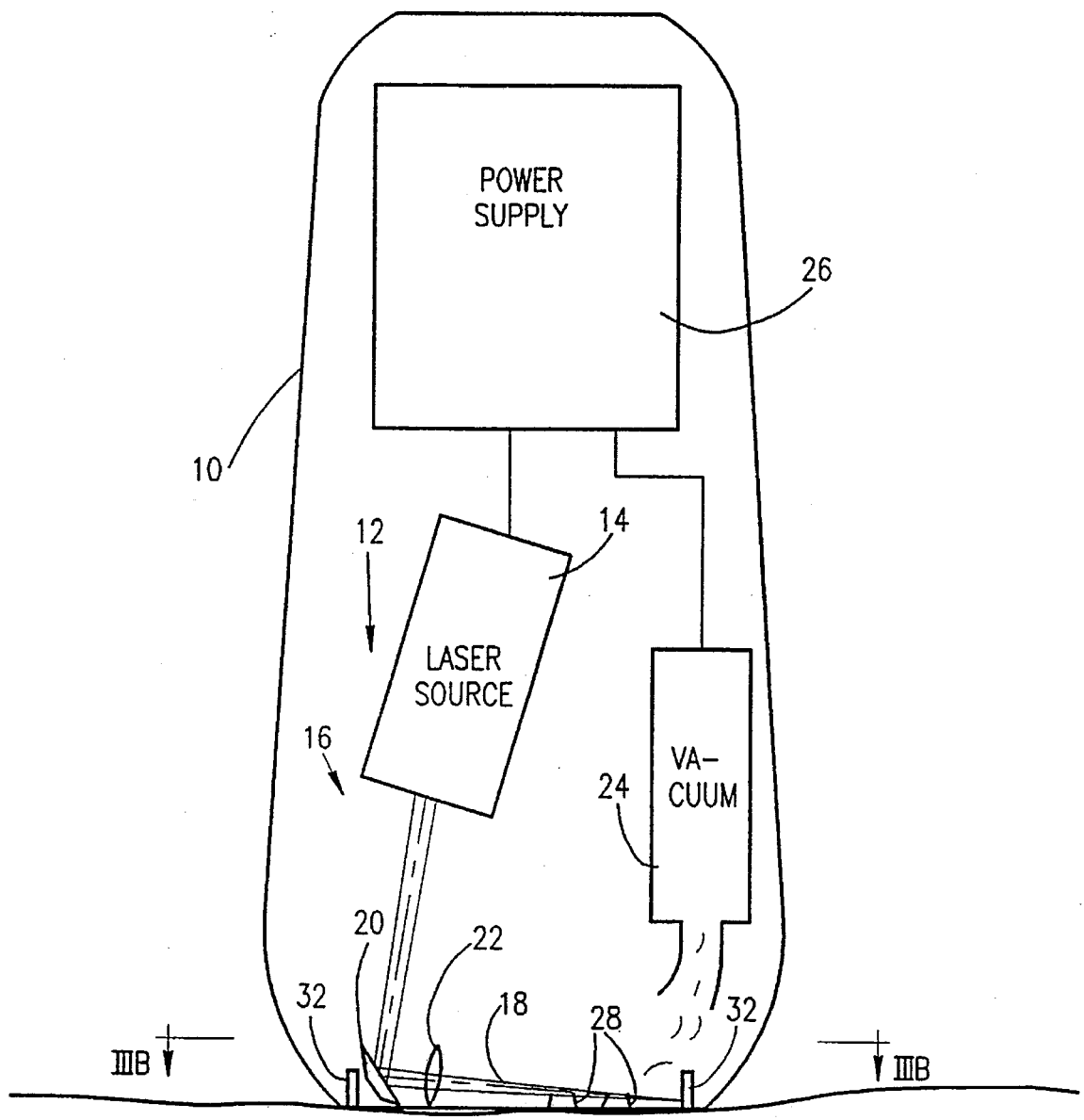
FIG. 3A is a simplified sectional illustration of a laser shaver constructed and operative in accordance with another preferred embodiment of the present invention.
Figure 3B:
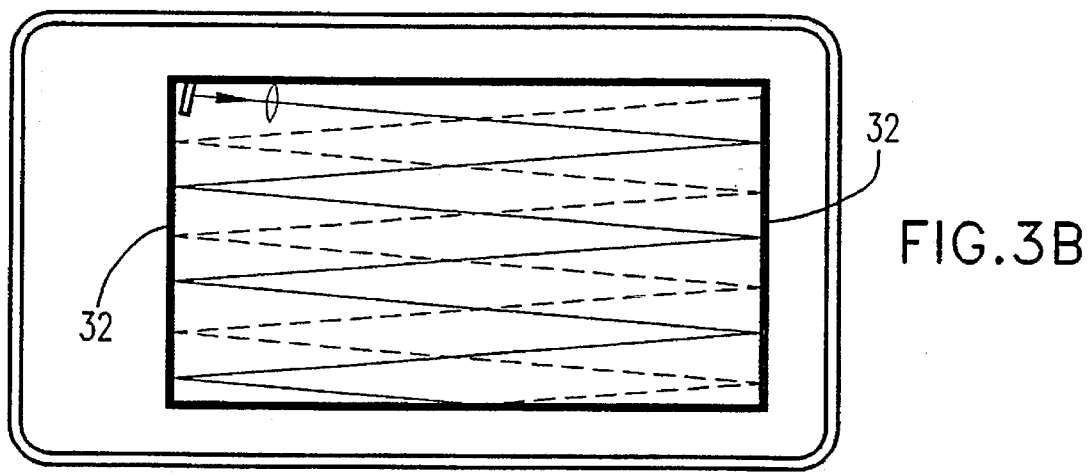
FIG. 3B is a simplified sectional illustration taken along the lines 3B—3B of FIG. 3A.

Reference is now made to FIGS. 3A and 3B which illustrate a preferred embodiment of laser shaver in which the laser beam transfer optics is designed to provide multiple reflections of the laser beam over a shaving region. In this case, the absorber 30 is replaced by at least two mirrors 32 and preferably a generally rectangular circumferential mirror assembly which is operative to provide a back and forth pattern of laser beams, which can be effective for cutting hair over a relatively large area. It is appreciated that in this embodiment, initial impingement of the laser beam on mirror 20 is such as to produce a reflection which is not perpendicular to the planes of mirrors 32.

According to a preferred embodiment of the present invention, there is provided apparatus for collecting loose hairs, which are cut by the impingement thereon of laser beam 18. The apparatus for collecting loose hairs preferably comprises electrically operated vacuum apparatus 24, such as a suction blower but may alternatively comprise any other suitable hair collection apparatus, such as electrostatic apparatus.

Both the laser source 12 and the vacuum apparatus may receive electric power from a suitable power supply 26, which may be battery powered or alternatively powered by an external source of current.

Figure 4:
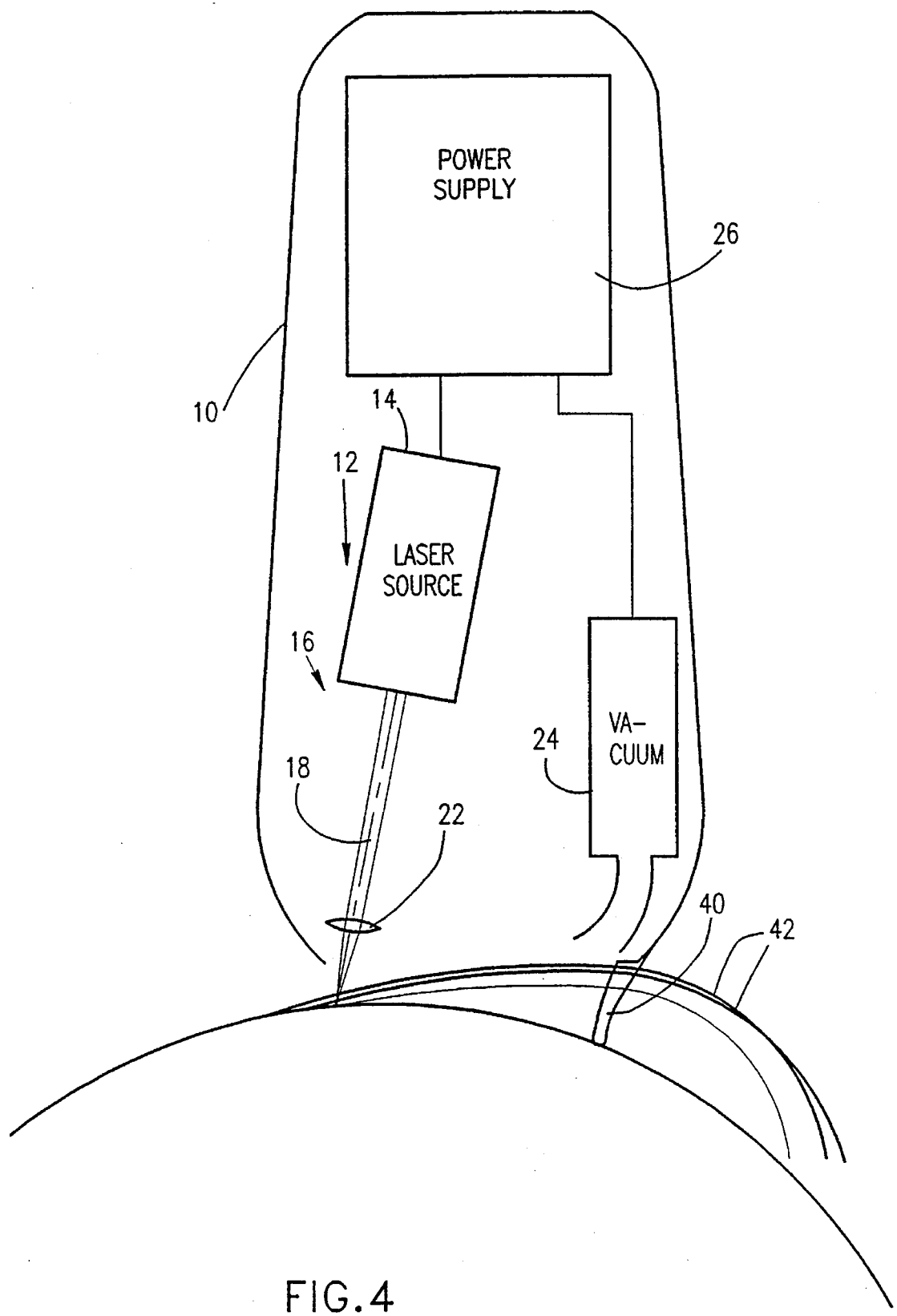
FIG. 4 is a simplified sectional illustration of a laser hair cutter constructed and operative in accordance with another preferred embodiment of the present invention.

Reference is now made to FIG. 3, which illustrates hair cutting apparatus constructed and operative in accordance with a preferred embodiment of the present invention and comprising many of the same elements as in the embodiment of FIGS. 2A, 2B, 3A and 3B, which are indicated by identical reference numerals. In the embodiment of FIG. 4, there is provided a comb portion 40 which arranges the hairs 42 on a person's head, generally in a plane so that they can be impinged upon a laser beam 18, which may be focussed thereon by a lens 22. Alternatively lens 22 may be eliminated. As a further alternative additional optical apparatus may be provided for positioning or configuring the laser beam, directing it along multiple paths or effecting scanning thereof.

It is a particular feature of the embodiment of FIG. 4, that color specific cutting may be provided, thus enabling white or gray hairs to be automatically cut, while leaving uncut dark colored hair. Additionally or alternatively, a hair thinning function may be provided, whereby only a desired percentage of all hairs may be cut by the laser beam.

It will be appreciated by persons skilled in the art that the present invention is not limited to what has been particularly shown and described hereinabove. Rather the scope of the present invention is defined only by the claims which follow:

I claim:

1. Hair cutting apparatus comprising:

a housing having an opening for hair, which is attached to the skin of a person, to be cut;

a source of laser radiation producing a laser beam substantially parallel to the surface of the skin to which the hair is attached, the laser beam being arranged to impinge on the hair and to cut the hair at a point of impingement only, leaving a portion of the hair in a detached unburnt condition and a further portion of the hair in an attached unburnt condition at the surface of the skin; and a vacuum hair collection device for collecting hair in a detached unburnt condition.

* * * * *